(12) United States Patent
Wartini et al.

(10) Patent No.: US 7,247,753 B2
(45) Date of Patent: Jul. 24, 2007

(54) METHOD FOR PRODUCING MACROCYCLIC KETONES BY MEANS OF DIECKMANN CODENSATION IN THE GAS PHASE

(75) Inventors: Alexander Wartini, Heidelberg (DE); Klaus Ebel, Lampertheim (DE); Gisela Hieber, Heidelberg (DE); Hagen Weigl, Ladenburg (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 10/519,549

(22) PCT Filed: Jul. 10, 2003

(86) PCT No.: PCT/EP03/07455

§ 371 (c)(1),
(2), (4) Date: Dec. 28, 2004

(87) PCT Pub. No.: WO2004/009524

PCT Pub. Date: Jan. 29, 2004

(65) Prior Publication Data

US 2005/0256341 A1    Nov. 17, 2005

(30) Foreign Application Priority Data

Jul. 18, 2002   (DE)   ................... 102 32 750

(51) Int. Cl.
   *C07C 45/67*   (2006.01)
(52) U.S. Cl. ............... 568/355; 568/356; 568/375
(58) Field of Classification Search ............... None
   See application file for complete search history.

(56) References Cited

U.S. PATENT DOCUMENTS

| 1,702,842 A | 2/1929 | Ruzicka |
| 1,702,843 A | 2/1929 | Ruzicka |
| 4,335,261 A | 6/1982 | Ueda ............... 568/366 |

FOREIGN PATENT DOCUMENTS

| EP | 0 251 111 | 1/1988 |
| EP | 0 352 674 | 1/1990 |
| EP | 0 400 509 | 12/1990 |

OTHER PUBLICATIONS

Renz et al. Ketonization of Carboxylic Acids by Decarboxylation: Mechanism and Scope; European Journal of Organic Chemistry, 2005, p. 979-988.□□.*
Organic Chemistry, 3rd Edition, Fieser and Fieser, 1956, p. 318.*
Tsuji, Jiro et al. "Application of Olefin Metathesis to Organic Synthesis. Syntheses of Civetone and Macrolides", Tetrahedron Letters, vol. 21, pp. 2955-2958 1980.
Choo, Yuen-May et al. "Synthesis of Civetone from Palm Oil Products", JAOCS, vol. 71, No. 8, pp. 911-913 1994.
Bost, Howard W. et al. "Cycloheptadecanone from Dimethyl Octadecanedioate via a One-Step Catalytic Process", Perfumer & Flavorist, vol. 7, p. 57 1982.

* cited by examiner

*Primary Examiner*—Sikarl A. Witherspoon
(74) *Attorney, Agent, or Firm*—Oblon, Spivak, McClelland, Maier & Neustadt, P.C.

(57) ABSTRACT

The invention relates to a method for producing macrocyclic ketones of general formula (I) by direct cyclisation of compounds of general formula (II) in the gas phase on a heterogeneous catalyst. In general formula (I), X represents a monounsaturated or polyunsaturated or saturated $C_{10}$–$C_{17}$ alkyl radical which can be optionally substituted by a $C_1$–$C_6$ alkyl radical, and in general formula (II), $R_1$, $R_2$ can respectively be the same or different and represent hydrogen or $C_1$–$C_6$ alkyl, and has the above-mentioned designation.

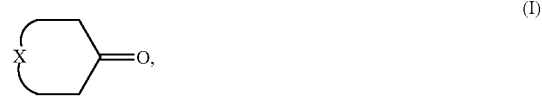

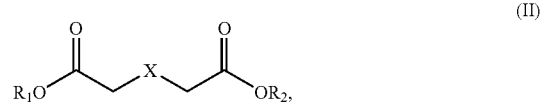

18 Claims, No Drawings

METHOD FOR PRODUCING MACROCYCLIC KETONES BY MEANS OF DIECKMANN CODENSATION IN THE GAS PHASE

CROSS-REFERENCE TO RELATED APPLICATIONS

The present application is a 371 application of PCT/EPO3/08455 filed Jul. 10, 2003.

The present invention relates to a process for the preparation of macrocyclic ketones ($C_{13}$–$C_{20}$) by Dieckmann condensation in the gas phase over a heterogeneous catalyst. The process is used particularly in the production of fragrances, for example civetone and exaltonee, which are used widely in the perfume and cosmetics industry.

The synthesis methods used hitherto are mostly based on a conventional intramolecular condensation reaction, such as the Dieckmann condensation in the liquid phase.

The synthesis of, for example, civetone by Dieckmann cyclization of 9-octadecene-1,18-dicarboxylic dialkyl esters and subsequent saponification and decarboxylation of the correspondingly obtained β-keto ester has been known for a long time (e.g.: J. Tsuji, Tetrahedron Lett., 21, 2955–2958 (1980); Y. Choo, J. Am. Oil Chem. Soc. 71, 911–913 (1994)).

H. W. Bost (Perfumer & Flavorist, 1982, 7, 57) describes a reaction of a saturated diester in the gas phase over a thorium oxide catalyst. However, the yields, at 14%, are markedly lower than in the customary cyclizations with high dilution.

The hitherto known methods for the preparation of macrocyclic ketones from linearly terminal diesters, however, have the following serious disadvantages:

1) It is necessary to use a strong base in a stoichiometric amount.
2) In order to achieve good yields the reaction has to be carried out with high dilution.
3) The β-keto ester which forms as an intermediate has to be saponified and decarboxylated in a separate step.
4) In the gas-phase reaction, extremely low yields are achieved. The catalyst used is expensive.

It is an object of the present invention to develop a preparation process for macrocyclic ketones which permits a simplified more economical mode of preparation.

We have found that this object is achieved according to the invention by a process for the preparation of macrocyclic ketones of the formula I

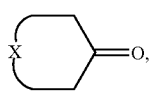
(I)

where

X is a mono- or polyunsaturated or saturated $C_{10}$–$C_{17}$-alkyl radical which may optionally be substituted by a $C_1$–$C_6$-alkyl radical, by direct cyclization of compounds of the formula II

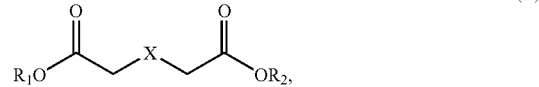
(II)

where $R_1$, $R_2$, in each case independently of the other, may be identical or different and are hydrogen or $C_1$–$C_6$-alkyl and X has the meaning given above, in the gas phase over a heterogeneous catalyst.

In this process, the linearly terminal dicarboxylic acids, monoester monocarboxylic acids or the dialkyl esters of the formula II are evaporated and cyclized directly to give the ketone in the gas phase over heterogeneous catalysts.

A mono- or polyunsaturated or saturated $C_{10}$–$C_{17}$-alkyl radical is understood as meaning, for example, a —$(CH_2)_{12}$—
—$(CH_2)_{14}$—
—$CH(CH_3)$—$(CH_2)_{11}$—
—$CH$=$CH$—$(CH_2)_8$—$CH$=$CH$—
$CH_2$—$CH_2$—$CH$=$CH$—$(CH_2)_6$—$CH$=$CH$—$CH_2$—$CH_2$—
—$(CH_2)_6$—$CH$=$CH$—$(CH_2)_6$— or a
—$CH_2$—$CH_2$—$CH$=$CH$—$(CH_2)_8$—$CH_2$—$CH$=$CH$—$CH_2$— radical, preferably a —$(CH_2)_{12}$— or a —$(CH_2)_6$—$CH$=$CH$—$(CH_2)_6$— radical.

A $C_1$–$C_6$-alkyl radical is understood as meaning, unless stated otherwise, a straight-chain or branched alkyl radical having 1 to 6 carbon atoms. Preference is given to the methyl, ethyl, n-propyl, isopropyl, n-butyl, t-butyl, pentyl or the hexyl group.

In a preferred embodiment, the fragrances exaltonee (cyclopentadecanone) or civetone (cis-9-cycloheptadecen-1-one) are prepared by the process according to the invention.

The compounds of the formula II are prepared by methods known per se, as are described in the literature (e.g. JAOCS, Vol. 71, No. 8 (1994), pp. 911–913 or Tetrahedron Lett. Vol. 21, (1980), pp. 2955–2958)), under reaction conditions as are known and suitable for the synthesis. In this connection, use may also be made of variants known per se which are not mentioned in more detail here.

The starting materials of the compounds of the formula II may, if desired, also be further reacted in situ without prior isolation of the compounds of the formula II directly to give the compounds of the formula I.

The advantage of the process according to the invention is that the cyclization, saponification and subsequent decarboxylation steps which are normally customary in a Dieckmann condensation carried out in solution take place in a single step in the gas phase, without isolation of the respective intermediates. A further advantage is that less solvent is required, which leads to a cost advantage and a reduced amount of waste which may have to be worked up.

The process can be carried out either in a fluidized bed or in a fixed bed. However, preference is given to carrying out the reaction in a fixed bed.

The cyclization is carried out at temperatures of from 200 to 600° C., preferably 250 to 500° C. In principle, the reaction is possible under reduced pressure, at atmospheric pressure or under increased pressure. To make it easier to evaporate the high-boiling starting materials, the reaction is preferably carried out under reduced pressure or at atmospheric pressure.

The reaction may be carried out with the addition of small amounts of water in order, after the cyclization, to favor ester hydrolysis steps. In this connection, the water can be added in one portion or in two or more steps at any desired point in the process, but before the mixture has completely passed the catalyst (e.g. if II already comprises water or water is added in the evaporator).

Suitable catalysts for the process according to the invention are all heterogeneous catalysts which comprise active components which are able to convert carboxylic acids, carboxylic esters or nitriles to ketones in the gas phase. Examples of such active components are oxides, hydroxides or carboxylates of subgroups I-VIII, or of main groups II, III and IV. Preference is given to using oxides, hydroxides or carboxylates of subgroups I to VIII, particularly preferably those of subgroup IV. The catalysts are often also doped with further components (e.g. oxides of main group I) and can be used either as unsupported catalyst or as supported catalysts. Suitable support materials are materials customary in catalyst chemistry, for example $SiO_2$ or $Al_2O_3$.

It is particularly advantageous to use $TiO_2$, in particular $TiO_2$ doped with alkali metal oxides or alkaline earth metal oxides, i.e. $TiO_2$ comprising about 2 to 10% by weight of $Na_2O$ and/or $K_2O$.

The catalysts are prepared in accordance with the processes described in EP 352 674.

To carry out the process, the compound II in the form of a liquid or a melt or a solution in an inert organic solvent, for example toluene or tetrahydrofuran is evaporated and then passed, optionally in the presence of an inert gas or mixtures of different inert gases, such as nitrogen, carbon dioxide or helium, at the desired reaction temperature in gaseous form over the catalyst arranged in a fixed manner or through a gas stream of fluidized catalyst. In order, after the cyclization, to favor ester hydrolysis steps, the reaction can be carried out with the addition of small amounts of water. Preference is given to working with 0 to 30% by weight of water, preferably with 5 to 15% by weight of water, based on the amount of II used.

The reaction products are condensed using suitable cooling devices, or precipitated with a suitable solvent (quench) and then fractionally distilled. Reaction products containing unreacted starting material can optionally be returned again directly to the cyclization reaction without further purification.

The process can be carried out continuously or as a batch process. Preference is, however, given to the continuous procedure.

The process according to the invention requires no stoichiometric amount of strong bases, no solvents or other auxiliaries and directly produces the macrocyclic ketones in good yields and selectivities.

EXAMPLES

Example 1

Preparation of exaltone from diethyl 1,16-hexadecanedioate

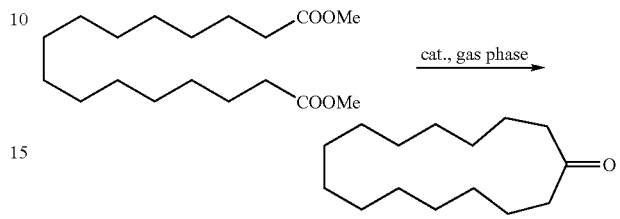

A solution of 10 g of diethyl 1,16-hexadecanedioate in 120 ml of tetrahydrofuran was evaporated in a gas-phase tubular reactor at 270° C. and passed with nitrogen at 350° C. over a catalyst ($TiO_2$+2% $K_2O$). Condensation and fractional distillation were then carried out. The yield was 78% with a selectivity of >90%.

Example 2

Preparation of civetone from dimethyl 1,18-octadec-9-enedicarboxylate

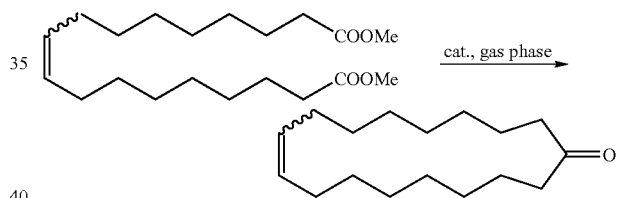

A solution of dimethyl 1,18-octadec-9-enedicarboxylate in toluene in a volume ratio of 1:9 was saturated with water until phase separation just no longer occurred. This solution was evaporated at 380° C. in a gas-phase tubular reactor and passed with nitrogen at 450° C. over a catalyst ($TiO_2$+2% $K_2O$). Condensation and fractional distillation were then carried out. The yield was 45% at a selectivity of 70%.

We claim:

1. A process for the preparation of macrocyclic ketones of the formula I

where
X is a mono- or polyunsaturated or saturated $C_{10}$–$C_{17}$-alkyl radical which may optionally be substituted by a $C_1$–$C_6$-alkyl radical,
said process comprising direct cyclization of a compound of the formula II

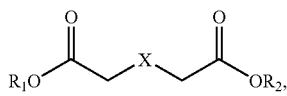

where
- $R_1$, $R_2$, in each case independently of the other, may be identical or different and are hydrogen or $C_1$–$C_6$-alkyl and X has the meaning given above, and wherein said cyclization takes place in the gas phase over a heterogeneous catalysts comprising, as active components, oxides, hydroxides or carboxylates of subgroups I to VIII, or of main groups II, III and IV, wherein the compound of formula (II) is evaporated and then passed at a desired reaction temperature in gaseous form over the catalyst arranged in a fixed bed.

2. The process as claimed in claim 1, wherein the reaction takes place at temperatures of from 200 to 600° C.

3. The process as claimed in claim 1, wherein the catalyst is a heterogeneous catalyst, comprising, as active components, oxides, hydroxides or carboxylates of subgroups I to VIII.

4. The process as claimed in claim 1, wherein the catalyst is a heterogeneous catalyst, comprising, as active components, oxides, hydroxides or carboxylates of subgroup IV.

5. The process as claimed in claim 1, wherein the catalyst is doped with oxides of main group I.

6. The process as claimed in claim 1, wherein the catalyst is $TiO_2$.

7. The process as claimed in claim 1, wherein the catalyst is $TiO_2$ doped with alkali metal oxides or alkaline earth metal oxides.

8. The process as claimed in claim 1, wherein the compound of the formula I is selected from the group consisting of exaltone and civetone.

9. The process as claimed in claim 1, wherein the compound of the formula II is selected from the group consisting of dimethyl 1,16-hexadecanedioate and dimethyl 1,18-octadec-9-enedicarboxylate.

10. The process as claimed in claim 1, wherein the reaction is carried out in the presence of from 0 to 30% by weight of water, based on the compound of the formula II.

11. The process as claimed in claim 2, wherein the catalyst is a fixed-bed catalyst.

12. The process as claimed in claim 2, wherein the catalyst is a heterogeneous catalyst, comprising, as active components, oxides, hydroxides or carboxylates of subgroups I to VIII, or of main groups II, III, and IV.

13. The process as claimed in claim 2, wherein the catalyst is a heterogeneous catalyst, comprising, as active components oxides, hydroxides or carboxylates of subgroups I to VII.

14. The process as claimed in claim 2, wherein the catalyst is a heterogeneous catalyst, comprising, as active components, oxides, hydroxides or carboxylates of subgroup IV.

15. The process as claimed in claim 2, wherein the catalyst is doped with oxides of main group I.

16. The process as claimed in claim 2, wherein the catalyst is $TiO_2$.

17. The process as claimed in claim 2, wherein the catalyst is $TiO_2$ doped with alkali metal oxides or alkaline earth metal oxides.

18. The process as claimed in claim 2, wherein the compound of the formula I is selected from the group consisting of exaltone and civetone.

* * * * *